United States Patent [19]
Semmlow et al.

[11] Patent Number: 5,722,419
[45] Date of Patent: Mar. 3, 1998

[54] SYSTEM FOR DETERMINING THE VIABILITY OF TISSUE

[76] Inventors: John L. Semmlow, 81 Lewis St., New Brunswick, N.J. 08901; Robert E. Brolin, 9 Sandburg Dr., Morganville, N.J. 07751-1428

[21] Appl. No.: 347,562

[22] Filed: Nov. 30, 1994

[51] Int. Cl.⁶ .................................................. H61B 15/05
[52] U.S. Cl. .......................... 128/733; 128/780; 128/741; 128/782
[58] Field of Search ..................... 607/7, 11, 48, 607/40, 52, 33; 128/642–644, 733, 782, 741, 780

[56] References Cited

U.S. PATENT DOCUMENTS

| | | | |
|---|---|---|---|
| 4,595,018 | 6/1986 | Rantala | 128/733 |
| 4,671,287 | 6/1987 | Fiddian-Green | |
| 4,781,197 | 11/1988 | Fukuda | 128/644 |
| 4,823,804 | 4/1989 | Ghislaine et al. | |
| 4,887,610 | 12/1989 | Mittal | |
| 5,012,820 | 5/1991 | Meyer | |
| 5,131,401 | 7/1992 | Westenskow et al. | 128/741 |
| 5,218,970 | 6/1993 | Turnbull et al. | 128/782 |
| 5,259,388 | 11/1993 | Eisman et al. | |
| 5,344,438 | 9/1994 | Testerman et al. | 607/118 |

FOREIGN PATENT DOCUMENTS

| | | |
|---|---|---|
| 1220-641 | 6/1981 | U.S.S.R. |
| WO 91/03272 | 3/1991 | WIPO |

*Primary Examiner*—Robert Nasser
*Attorney, Agent, or Firm*—Klauber & Jackson

[57] ABSTRACT

When human intestine becomes damaged due to insufficient blood perfusion (ischemic disease), the damaged tissue must be surgically removed and the remaining tissue sewn together (end-to-end anastomoses). If nonviable tissue is not removed the result can be fatal while removal of too much bowel can also lead to severe complication. The distinction between viable and nonviable tissue must often hastily be made during urgent operations on critically ill patients. This decision remains a challenge for even the most experienced general surgeon. The system disclosed herein is a medical instrument designed to quantify the survivability of intestine compromised by ischemic disease. This medical instrument evaluates ischemic tissue through the quantification of electrical and contractile activity. The computer-based instrument uses advanced signal processing techniques to remove measurement artifact and physiological variability. It provides the surgeon with immediate information that is useful in predicting long-term bowel viability allowing him to remove (resect) an optimal segment of bowel.

30 Claims, 6 Drawing Sheets

20mA

50mA

100mA

SYSTEM FOR DETERMINING THE VIABILITY OF TISSUE

FIELD OF THE INVENTION

The present invention relates to a system for quantitative assessment of intestine compromised by ischemic disease and, more particularly, to a system which affords diagnostic information regarding the likelihood that a segment of intestine will be viable in the long-term. Such a system is intended for use in determining what segments of bowel should be removed during a surgical treatment of intestinal ischemic disease.

DESCRIPTION OF THE PRIOR ART

A variety of mechanisms can lead to reduction of afferent or efferent blood flow in the gastrointestinal tract and if the blood supply is reduced or occluded over a long period of time, the affected tissue may become irreversibly damaged or necrotic. Successful treatment of severely ischemic bowel requires removal of all nonviable tissue. However, the removal of too much bowel can lead to short bowel syndrome which can ultimately be fatal. Hence, important decisions must often be hastily made during urgent operations on critically ill patients.

Methods currently available for the assessment of bowel viability rely either on crude qualitative measures requiring subjective interpretation of visual features such as color, or on variables indirectly related to actual tissue viability such as the presence of local arterial blood flow. Such methods have been shown to be unreliable in predicting either the healing capability or long-term viability of an ischemic bowel. The following is a description of some of the aforesaid methods which have been patented, or other patented apparatuses and/or methods which are somewhat related to the present invention.

In World Patent No. 91/03272, Hognelid et al. disclose a medical appliance for stimulating and measuring tissue contractions. Specifically, a stimulation potential is applied to tissue so as to induce contractions while the contractions are measured by means of bipolar electrodes which interface with a computer. While it is stated by Hognelid et al. that contractions are measured by means of bipolar electrodes which interface with a computer, it is not stated that spontaneous electrical activity is measured by the electrodes as disclosed by the present invention.

In U.S. Pat. No. 5,012,820, Meyer discloses a device for determining a change in mechanical and/or electrical magnitudes during muscular contraction. Specifically, means are provided for exciting a muscle, via an electrical stimulation, so as to induce a muscle contraction, and means are provided for measuring the muscular contraction and electrical signals generated during the muscle contraction. The device disclosed by Meyer is described in terms of measuring skeletal musculature, and not to measuring both spontaneous electrical activity and contractions in an intestine as disclosed by the present invention.

In U.S. Pat. No. 4,887,610, Mittal discloses a device for measuring pressure changes and electrical changes in a sphincter. Specifically, a catheter comprising a pressure sensing means and an electrical sensing means is provided for simultaneously measuring pressure changes and electrical changes, respectively, in a sphincter. There are no means disclosed by Mittal for delivering an electrical stimulus to the sphincter, which is crucial to the function of the present invention.

In U.S. Pat. No. 5,259,388, Eisman et al. disclose an electrode assembly for simultaneously measuring myographic signals from proximal and distal muscles of the anal canal. Specifically, a first and a second pair of electrodes are displaced along an insulating support which fits within the anal canal so as to simultaneously measure myographic signals from proximal and distal muscles, respectively, of the anal canal. There are no means disclosed by Eisman et al. for delivering an electrical stimulus to the proximal and distal muscles, which is crucial to the function of the present invention.

In U.S. Pat. No. 4,823,804, Ghislaine et al. disclose an apparatus for monitoring the activity level of an organ of the human body. Specifically, a pair of differentially connected sensors positioned within the vicinity of an organ provide signals representative of the activity level of the organ to processing and display means. There are no means disclosed by Ghislaine et al. for delivering an electrical stimulus to the organ, which is crucial to the function of the present invention.

In U.S. Pat. No. 4,671,287, Fiddian-Green discloses an apparatus and method for sustaining intestinal vitality and for performing ischemia detection. Specifically, a medical treatment apparatus and method is disclosed wherein a catheter is positioned within an organ of the gastrointestinal tract so that the organ can be oxygenated and blood gas from the organ can be obtained and analyzed so as to detect incipient ischemia. There are no means disclosed by Fiddian-Green for delivering an electrical stimulus to the intestine or for measuring either electrically induced contractility or spontaneous electrical activity of the intestine, which is crucial to the function of the present invention.

In Soviet Union Patent No. 1220-641, a method is disclosed for determining the viability of a transplant after operation. Specifically, the viability of a transplant is determined by monitoring its biological potential via a capillary electrode. There are no means disclosed in this Soviet Union patent for delivering an electrical stimulus to the transplant, which is crucial to the function of the present invention.

At this point it should be noted that the citation of any reference herein should not be deemed an admission that such reference is available as prior art to the present invention.

Although all of the above-mentioned patents are directly or indirectly related to the subject matter of the present invention, none disclose an apparatus and/or method for evaluating the viability of ischemic tissue through the quantification of electrical and contractile activity. Such an apparatus and/or method would be desirable in assessing the long-term viability of bowel tissue. The present invention is directed toward such an apparatus and/or method.

SUMMARY OF THE INVENTION

The present invention contemplates a diagnostic system comprising a hand held probe capable of performing a measurement of the ability of the intestine to contract to a well controlled electrical stimulus and also a measurement of the spontaneous electrical activity of the bowel. It has been shown that of all currently known techniques to assess bowel viability, only electrically induced contractility and spontaneous electrical activity demonstrate statistically significant predictive abilities. Therefore, in this aspect of the invention, an electrical stimulus is delivered to the bowel which is precisely regulated by a control mechanism. The control mechanism, which is a small computer in the preferred embodiment, also quantifies the evoked contractile response as sensed by a transducer in the hand held probe. The control mechanism also records and quantifies the spontaneous electrical activity of the intestine which is sensed by electrodes in the hand held probe. In another aspect of this invention, signal processing techniques are applied to the spontaneous electrical activity in order to improve the diagnostic information supplied by the spontaneous electrical activity. In yet another aspect of this invention, a noise cancellation procedure is applied to the contractility signal to remove motion artifact due to respiration or other movement.

The application of the present invention is as a medical device to assess long-term survivability of bowel compromised by ischemic disease. A surgeon attaches the hand held probe to a small segment of bowel and activates the device. The control mechanism initiates a small electrical stimulus to the bowel, monitors the evoked mechanical response, and also monitors the spontaneous electrical activity. After processing and analyzing the monitored data, the control mechanism constructs and displays a number representing the likelihood of ultimate bowel survival. The surgeon then uses this information, along with similar information from surrounding tissue, to determine what tissue should be removed and what should be allowed to remain.

From the above descriptive summary it is apparent that the present invention provides an apparatus and/or method for evaluating the viability of ischemic tissue through the quantification of electrical and contractile activity. Such an apparatus and/or method would be desirable in assessing the long-term viability of bowel tissue.

Accordingly, the primary object of the present invention is to provide a quantitative, graded measure representative of the long-term survival of a given segment of intestine. Another object of the present invention is to provide such information in a timely fashion directly to a surgeon during a resection operation. A further object of the present invention is to provide such information through a relatively inexpensive, trouble free procedure, which does not require highly trained operating personnel.

Other objects and advantages of the present invention will become apparent to those skilled in the art upon reading the following detailed description and claims, in conjunction with the accompanying drawings which are appended hereto.

BRIEF DESCRIPTION OF THE DRAWINGS

In order to facilitate a fuller understanding of the present invention, reference is now be made to the appended drawings. The drawings should not be construed as limiting the present invention, but are intended to be exemplary only.

PREFERRED EMBODIMENT OF THE PRESENT INVENTION

Figure 1:
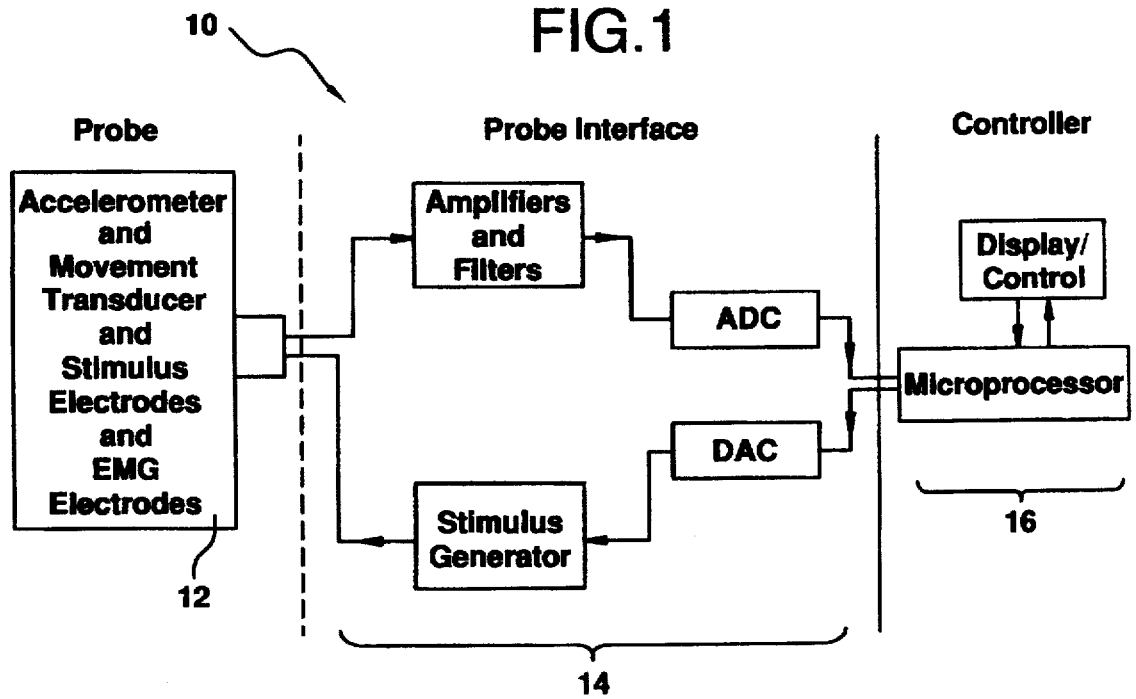
FIG. 1 is a block diagram of a medical instrument for evaluating the viability of ischemic tissue through the quantification of electrical and contractile activity according to the present invention.

Referring to FIG. 1, there is shown a schematic diagram of a medical instrument 10 for evaluating the viability of ischemic tissue through the quantification of electrical an contractile activity according to the present invention. The medical instrument 10, termed an Electromyographic and Contractility Monitor (ECM), comprises a measurement probe 12 which incorporates both electromyographic (EMG) and stimulus electrodes along with a strain gauge movement transducer to monitor contractile response and an accelerometer for sensing total probe motion. The medical instrument 10 also comprises a controller 16 for controlling electrical stimuli delivered by the probe 12 and for recording and analyzing contractile response and spontaneous electrical activity so as to generate a number representative of bowel survival. The controller 16 provides a display for illustrating the recorded and analyzed contractile response and electrical activity. The medical instrument 10 further comprises interface electronics 14 between the probe 12 and the controller 16. The interface electronics 14 comprise a digital-to-analog converter and a stimulus generator which act in combination to generate the electrical stimuli delivered by the probe 12. The interface electronics 14 also comprise an analog-to-digital converter and a plurality of amplifier and filter circuits which are serially connected so as to provide digital values to the controller 16 of sensed spontaneous electrical activity, tissue contractile response, and total probe motion. It should be noted that the controller 16 is typically PC-based with a keyboard for entering commands and a CRT for illustrating the recorded and analyzed contractile response and electrical activity. However, it should also be noted that the controller 16 may be a device solely dedicated to performing the functions of the present invention.

Figure 2:
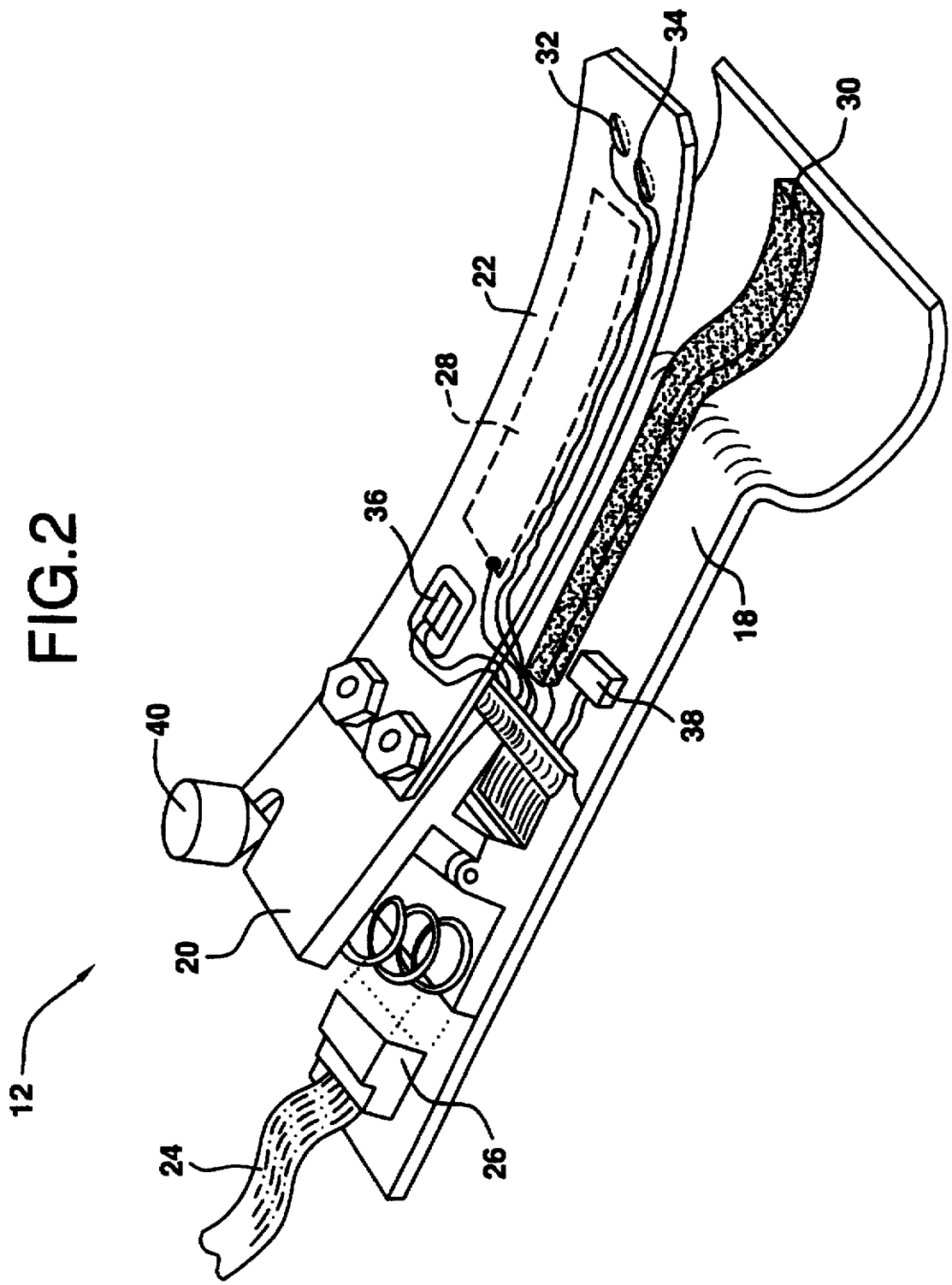
FIG. 2 is a first embodiment of a measurement probe used in the medical instrument described in FIG. 1.

Referring to FIG. 2, there is shown a first embodiment of the measurement probe 12 comprising a rigid support member 18, a spring-loaded clamp 20, a flexible support member 22, an electrical cable 24, an electrical connector 26, a pair of stimulus electrodes 28,30, a pair of EMG electrodes 32,34, a strain gauge movement transducer 36, and an accelerometer 38. The spring loaded clamp 20 is mounted directly on the rigid support member 18 along with the electrical connector 26, the first stimulus electrode 30, and the accelerometer 38. The flexible support member 22 is bolted securely to the spring loaded clamp 20, and the spring loaded clamp 20 is provided with a thumbscrew 40 for adjusting the tension of the flexible support member 22. The second stimulus electrode 28, the EMG electrodes 32,34, and the strain gauge movement transducer 36 are all mounted on the flexible support member 22. The rigid support member 18 is curved at one end so as to allow the tissue to be suitably gripped therein. The stimulus electrodes 28,30, the EMG electrodes 32,34, the strain gauge movement transducer 36, and the accelerometer 38 are all wired to the electrical connector 26 where they are connected to the interface electronics 14 via the electrical cable 24. In this embodiment, the strain gauge movement transducer 36 senses bending in the flexible support member 22 thus providing a measurement of movement in tissue clamped between the rigid support member 18 and the flexible support member 22.

Figure 3:
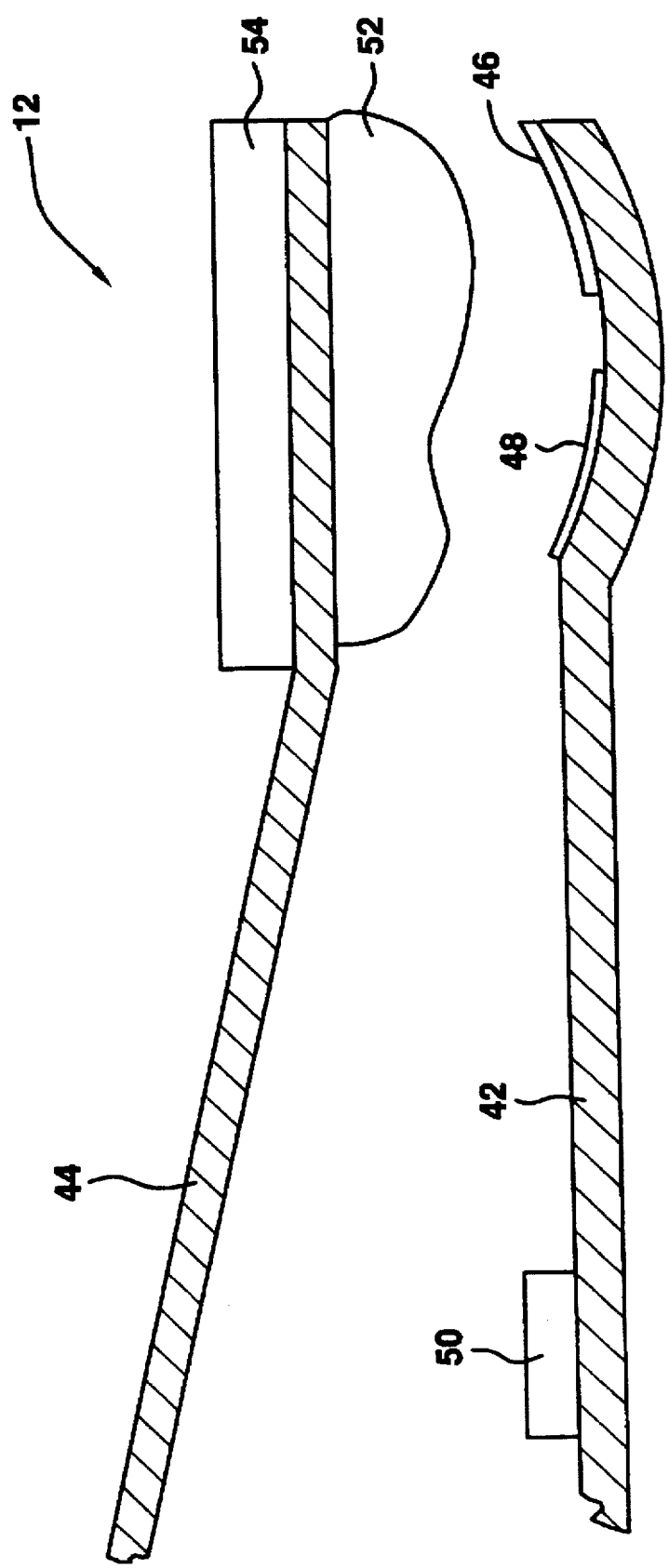
FIG. 3 is a second partial embodiment of a measurement probe used in the medical instrument described in FIG. 1.

Referring to FIG. 3, there is shown a second partial embodiment of the measurement probe 12 comprising a pair of rigid support members 42,44, a pair of stimulus electrodes 46, a pair of EMG electrodes 48, an accelerometer 50, a flexible fluid filled membrane 52, and a pressure transducer 54. The stimulus electrodes 46, the EMG electrodes 48, and the accelerometer 50 are all mounted on the first rigid support member 42. The flexible fluid filled membrane 52 and the pressure transducer 54 are mounted on the second rigid support member 44. Although not shown, the stimulus electrodes 46, the EMG electrodes 48, the accelerometer 50, and the pressure transducer 54 are all wired to an electrical connector where they are connected to the interface electronics 14 via an electrical cable 24, similar to the cable of the measurement probe 12 shown in FIG. 2. In this embodiment, the pressure transducer 54 senses pressure in the flexible fluid filled membrane 52 thus providing a measurement of movement in tissue clamped between the pair of rigid support members 42,44. This measurement probe more effectively accommodates a wide variety of bowel shapes and sizes than the previously described measurement probe (the diameter and shape of the bowel is highly variable depending on the current digestive state). Also, this measurement probe is sensitive to nearly all transverse contractile patterns and, indirectly, to most longitudinal contractions.

Referring again to FIG. 1, the controller 16 provides a digital signal, representative of the value of an electrical stimulus, to the digital-to-analog converter. In turn, the digital-to-analog converter converts the digital signal into a voltage-based analog pulse train signal which is fed into a stimulus generator circuit. The stimulus generator circuit converts the voltage-based analog pulse train signal into a constant current stimulus pulse train which is sent to the stimulus electrodes on the measurement probe 12. It should be noted that typically one of the stimulus electrodes is grounded so that the other stimulus electrode can apply both positive and negative (or bipolar) constant current stimulus pulses to the clamped tissue.

Figure 4:
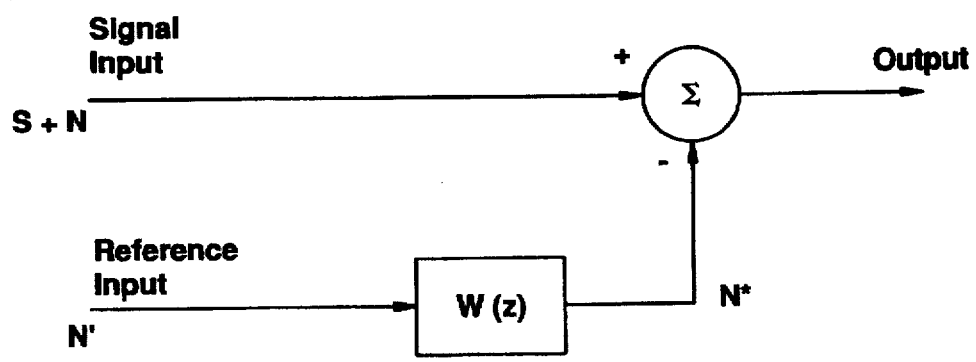
FIG. 4 is a schematic representation of an adaptive noise cancellation approach.

In both of the above-described measurement probes 12, the accelerometers 38,50 are used to sense total probe motion. Relatedly, an important aspect of the present invention is the use of an Adaptive Noise Cancellation (ANC) procedure to reduce artifact due to respiration (or other artifact due to probe motion). The outputs from the accelerometers 38,50 serve as a reference signal which is used to reduce the influence of motion artifact on the contractile signal through an adaptive noise cancellation approach. Referring to FIG. 4, there is shown a schematic representation of such an adaptive noise cancellation approach. Essentially, a modified artifact signal, N*, is subtracted from the contractile plus artifact signal, S+N, by a weighted subtraction procedure. A key feature in this approach is the application of an adaptive filter to the reference signal, N', so as to produce the modified artifact signal, N*, which most closely matches the actual artifact signal, N, present in the contractile signal plus artifact signal, S+N.

Figure 5A:
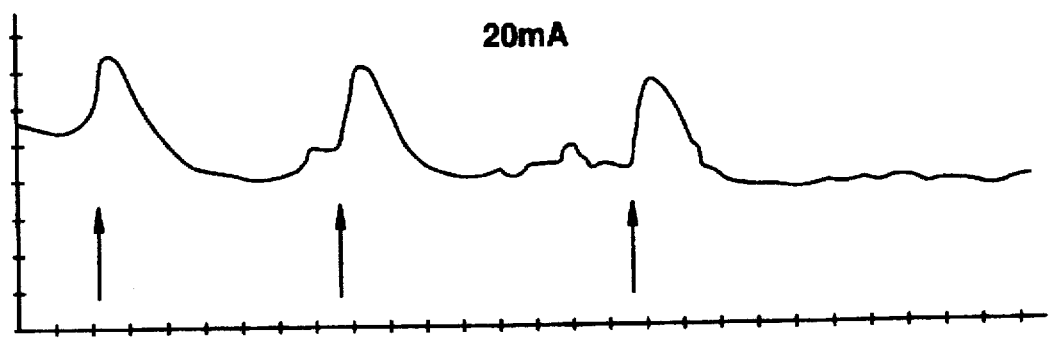
FIG. 5A shows a normal contractile response waveform of normal tissue.
Figure 5B:
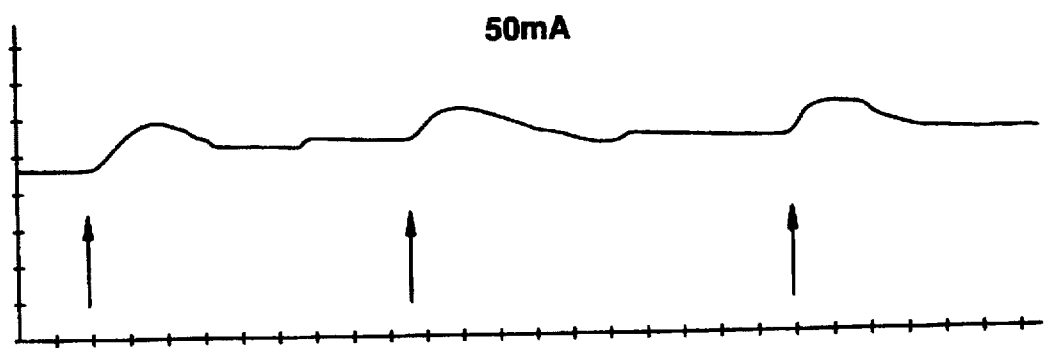
FIG. 5B shows a normal contractile response waveform of mildly ischemic tissue.
Figure 5C:
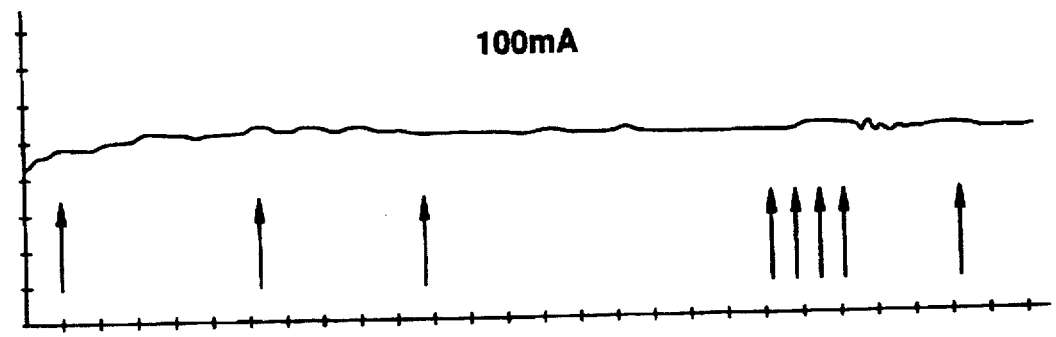
FIG. 5C shows a normal contractile response waveform of necrotic tissue.

Another aspect of the present invention is the use of a specially designed procedure to quantify the contractile signal. This procedure takes advantage of the known dynamic characteristics of a normal contractile response (see FIGS. 5A, 5B, and 5C) by applying a weighted subtraction procedure or a form of template matching to the noise canceled contractile signal. This weight function, utilizing a template determined empirically, is applied to the rectified, noise canceled contractile response so that responses which follow the normal time course pattern are emphasized. After weighing, the RMS value of the weighed, rectified, noise canceled contractile response is calculated to quantify the contractile response.

Another important aspect of the present invention is the use of signal processing techniques to reduce the variation in spontaneous electrical activity (EMG) due to the aberrancy in the natural cyclic rhythms that occur during periods of ischemia. Two different techniques are employed to compensate for these natural variations in EMG activity: 1.) isolation of EMG slow wave components; and 2.) elimination of less stable frequency components. Isolation of the electrical slow wave components removes the influence of the large spikes (which represent smooth muscle contractions) which tend to be inherently intermittent even in normal bowel. To separate the two EMG components, a template matching method is used in which a spike template is created from known temporal spike characteristics. This template is applied to the EMG signal and is used to identify spike occurrences. Since spikes are much shorter in duration than slow waves, they are easily dissected out from the EMG signal once identified.

Yet another important aspect of the invention is the use of bandlimiting filtering to eliminate frequencies which are known to be susceptible to physiological variation. These more variable frequency components have been determined from analysis of long-term recordings of EMG signals in normal and ischemic tissue.

EXPERIMENTAL RESULTS

INTRODUCTION

Intraoperative evaluation of intestinal viability has traditionally relied upon gross visual features such as bowel color, presence of visible peristalsis, and bleeding from a cut edge of a bowel. More recently, objective methods of intestinal viability assessment such as Doppler ultrasound and fluorescein fluorometry have been used in clinical settings. The present invention Electromyographic and Contractility Monitor (ECM) was introduced as a quantitative method of measuring contractile activity in ischemic bowel. The ECM consists of two major components, a specially designed probe and an electronic control unit which includes computer-assisted data acquisition. The probe is used to electrically stimulate bowel tissue and then measure both evoked contractile response and spontaneous electrical activity (EMG) in response thereto.

The present study was undertaken to evaluate quantified measurements which were taken with the present invention ECM in the assessment of bowel viability and then to compare these measurements with other qualitative and objective methods of bowel viability assessment. These other qualitative methods included visual assessment of bowel color and presence of peristalsis. These other objective methods included Doppler ultrasound, threshold stimulus level (TSL) measured by the ECM, and reflection densitometry. Reflection densitometry provided a quantitative measurement of bowel color in the red and blue spectrum.

MATERIAL AND METHODS

Figure 6:
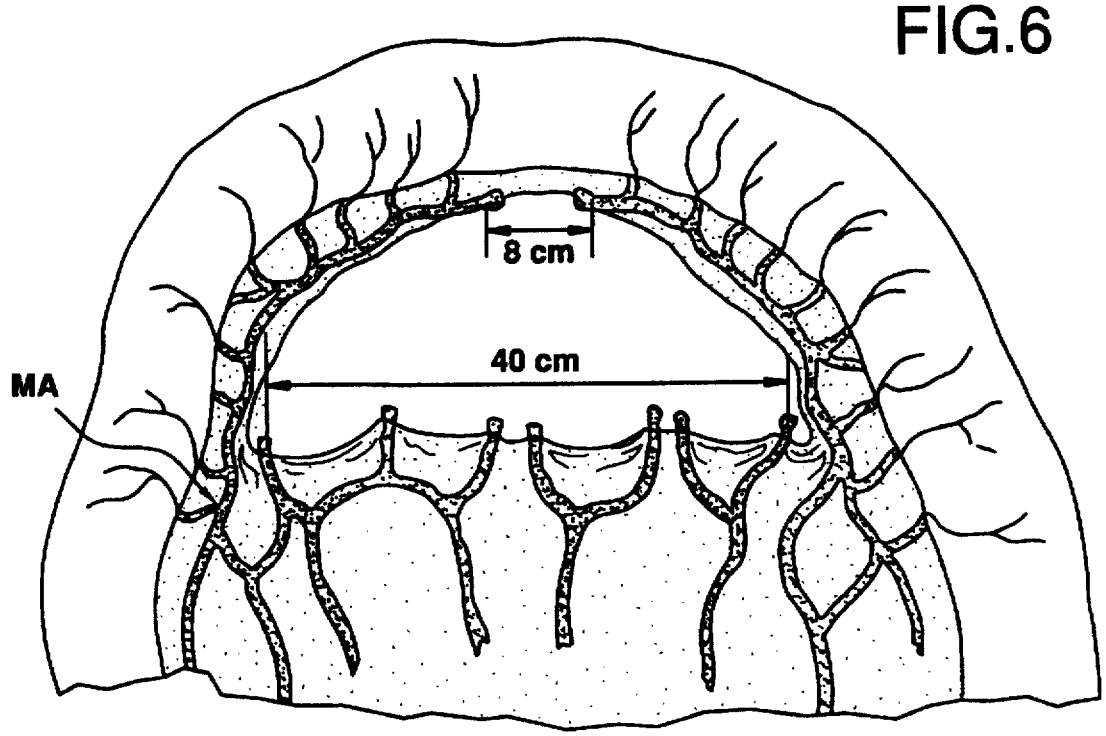
FIG. 6 shows a segment of an intestine prior to undergoing a laparotomy and a selective mesenteric arterial ligation to devascularize a 40 cm segment of distal ileum.

Thirty-one adult mongrel dogs underwent laparotomy and selective mesenteric arterial ligation to devascularize a 40 cm segment of distal ileum. Referring to FIG. 6, the mesenteric arterial supply to the distal ileum was litigated for a distance of 40 cm and the marginal artery (MA) in the center of the ischemic segment was then suture litigated proximally and distally for a distance of 8 cm, thus depriving that length of bowel of all collateral flow. A gradation of ischemic damage was consistently exhibited along the 40 cm segment of intestine, varying from normal-appearing bowel at the outer margins to gangrenous intestine at the midpoint. After 24 hours, each animal underwent relaparotomy. At the second laparotomy, measurements were taken at 2 cm intervals along the 40 cm ischemic segment. Measurements were also taken from normal bowel beyond the proximal and distal boundaries of the 40 cm ischemic segment.

Peristalsis was induced by squeezing the intestine between the thumb and index finger and was recorded as present or absent at each 2 cm interval. Visual assessment of bowel color was made by one observer to maintain consistency throughout the study and was recorded at each 2 cm interval according to the following criteria: 1.) pink intestine appeared clearly viable and was indistinguishable in color from bowel outside of the 40 cm ischemic segment; 2.) dusky bowel was slightly cyanotic and clearly darker than normal intestine; 3.) blue bowel was moderately cyanotic; and 4.) black bowel appeared grossly necrotic. Doppler ultrasound readings were recorded by one observer as presence or absence of an audible pulsatile signal in the marginal artery at each 2 cm interval.

A quantitative assessment of intestinal color was determined by reflection densitometry using a portable color reflection densitometer (Model RCP by Tobias Associates, Inc. Ivyland, Pa.). This densitometer is a hand-held device that shines a light on the serosal surface of the bowel and measures the amount of reflected light which can be broken up into red, green, and blue portions of the visible spectrum. A low reading on the densitometer indicates that a higher percentage of light is reflected rather than absorbed whereas a high reading implies a minimal amount of light reflection. Measurements at each site were obtained within approximately 2 seconds. The red and blue spectra were arbitrarily chosen for evaluation because these two colors closely correspond to the changes in color that are observed in progressively ischemic bowel. In order to evaluate consistency, two measurements were recorded for each spectrum at 2 cm intervals within the ischemic segment. The mean of these two measurements was used in the data analysis.

Figure 7:
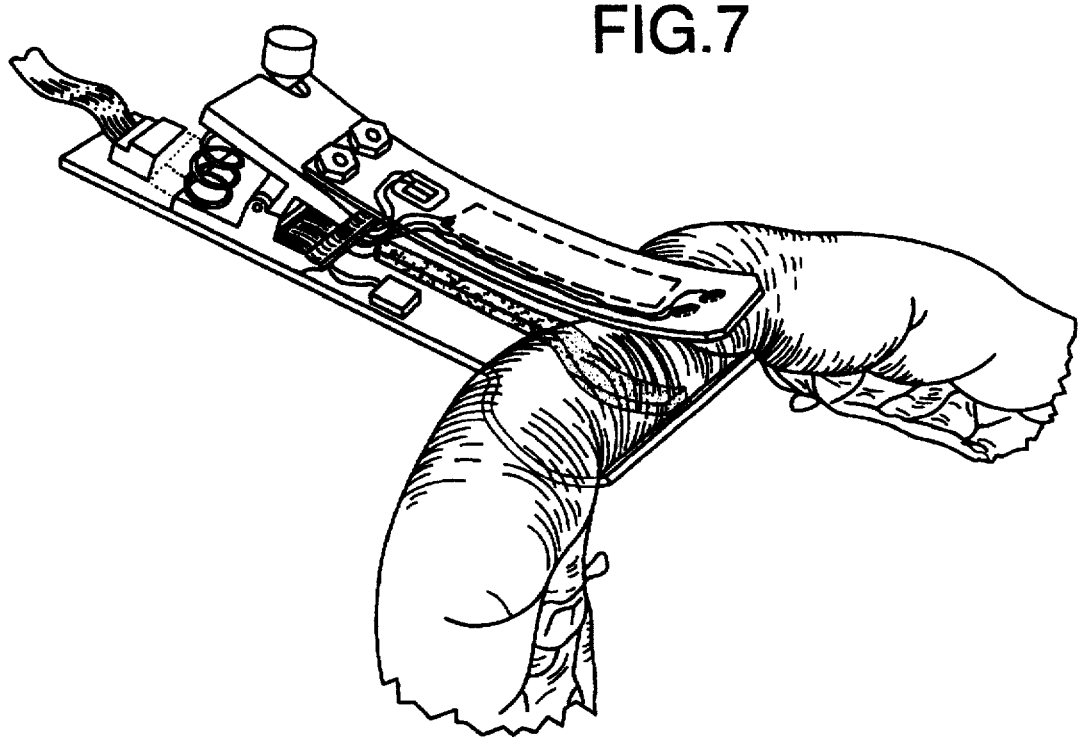
FIG. 7 shows a segment of bowel being gripped by a measurement probe according to the present invention.

Myoelectric assessment of bowel viability was performed using the ECM. As shown in FIG. 7, the probe was clipped onto the serosal surface of the bowel and measurements were obtained. Stainless steel electrodes, located on the top and bottom plates of the probe, delivered a constant current biphasic stimulus to the bowel wall. The maximum stimulus current delivered by the probe was 100 mA. The contractile response was measured by the strain gauge movement transducer, which includes two strain gauges that are bonded to the flat section of the upper arm. The strain gauges recorded both longitudinal and transverse motion of the bowel wall. The remaining electrical circuitry of the ECM is as previously described.

TSL is defined as the minimum stimulus in milliamps (mA) that can elicit a clearly defined smooth muscle contraction on a strip chart recorder. The TSL value is determined by serially stimulating the bowel at varying magnitudes of current until the minimum stimulus current required to elicit a contractile response is obtained. Consequently, multiple stimulations at each 2 cm interval are required to determine the TSL.

Figure 8A:
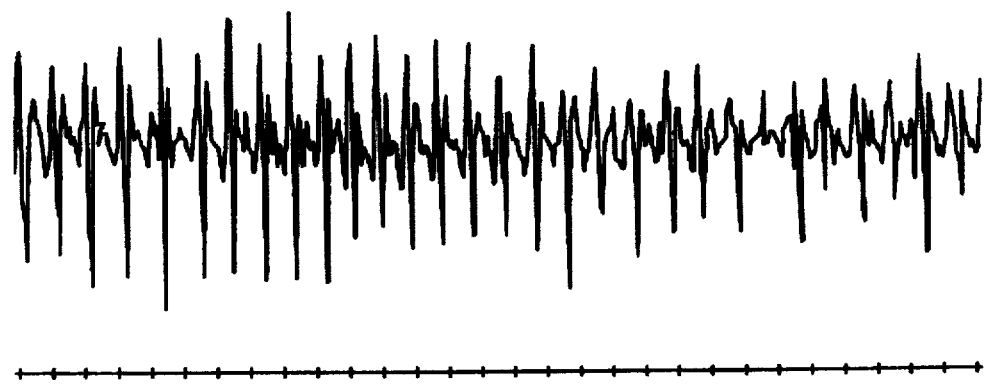
FIG. 8A shows an EMG recording in a normal bowel.
Figure 8B:
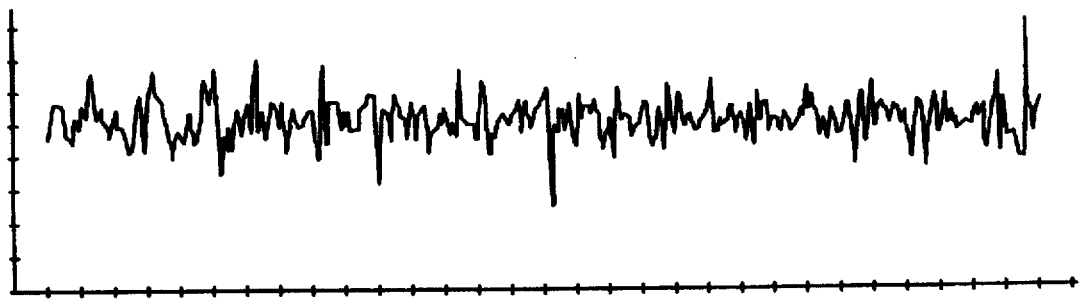
FIG. 8B shows an EMG recording in a mildly ischemic bowel.
Figure 8C:
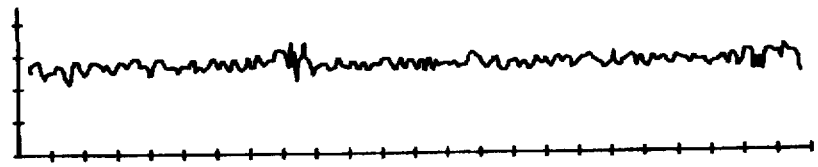
FIG. 8C shows an EMG recording in a necrotic bowel.

EMG recordings in normal, ischemic, and necrotic bowel are shown in FIGS. 8A, 8B, and 8C, respectively. The computer algorithm in the ECM was designed to quantify the EMG by computing the average root mean square (rms) value of the EMG over a 10 second time interval. Hence, this measurement combines intestinal slow wave amplitude and spike activity which comprise the EMG. The quantified EMG is expressed in millivolts (mY). The EMG was always recorded before electrical stimuli were delivered to the bowel in order to avoid stimulation-induced distortion of baseline EMG activity.

EMG and reflection densitometry data were analyzed as mean values of the raw data and as normalized values. Use of normalized measurements accounted for the variance in measurements recorded in normal bowel proximal and distal to the 40 cm ischemic segment. The normalized densitometry data were derived by dividing measurements obtained at each 2 cm interval by the mean values obtained in normal bowel beyond the proximal and distal boundaries of the 40 cm ischemic segment. Unnormalized data were used for reflection densitometry measurements because there was no difference between measurements recorded in the normal bowel proximal and distal to the ischemic segment. Conversely, proximal- and distal-normalized measurements were used for expressing the EMG data because the EMG in normal bowel distal to an area of severe ischemic damage is expected to be inherently different than the EMG in the proximal normal bowel. Normalized EMG measurements were calculated by dividing the EMG measurements obtained at each 2 cm interval by the respective values obtained in normal bowel proximal and distal to the ischemic segment. Hence, the normalized EMG measurements are expressed as percentage values.

The 31 dogs were comprised of three groups according to arbitrarily selected thresholds of EMG which determined the site of resection and anastomosis. In the first group resection was performed at the site closest to an EMG measurement that corresponded to 25% of the EMG measurement in normal bowel. In the second group resection was carried out at a point closest to an EMG that corresponded to 33% to the EMG measured in normal bowel. In the third group the bowel was resected at the site where the EMG corresponded to 50% of the EMG measured in normal bowel. There were 10 dogs in both groups 1 and 2 and 11 dogs in group 3. An extra dog was mistakenly added in group 3. Because the 11th dog in group 3 died and represented the only death in this group, this "extra" dog was included in order to not favorably misrepresent the results. All anastomoses were performed using an inner layer of continuous 3-0 polyglycolic acid suture and an outer layer of interrupted seromuscular 3-0 silk sutures. Dogs that survived were sacrificed 13 days after resection and anastomosis. At the time of sacrifice the anastomotic site was inspected in vivo and excised for measurement of bursting pressure using a standard pressure manometer which recorded intraluminal pressure up to 300 mm Hg in a closed system. Statistical analysis was performed using the $X^2$ test, the two-tailed paired and unpaired Student's t test, and a two-way analysis of variance (ANOVA).

RESULTS

There were nine deaths from anastomotic leaks, all due to further bowel necrosis. At the time of sacrifice there was no gross evidence of residual ischemia at the anastomoses of animals that survived. Bursting pressure measurements were greater than 300 mm $H_g$ in each of the 22 anastomoses that healed. Correlations between each method of intestinal viability assessment and outcome are shown in Table 1. Visual assessment of bowel color did not correlate with survival. In surviving animals, bowel color was pink at 17 resection margins, dusky at 24 margins, and blue at 3 margins. In dogs that died, 4 margins were pink, 11 were dusky, 1 was blue, and 2 were black. Peristalsis also did not correlate with survival. Peristalsis was visible at 40 of 44 resection margins in dogs that survived versus 16 of 18 resection margins in nonsurvivors.

TABLE 1

Correlations between Methods of Viability Assessment and Survival

| Method | Survivors | Deaths | Correlation |
|---|---|---|---|
| Intestinal Color | | | |
| Pink | 17 | 4 | $X^2 = 6.1, P = 0.11$* |
| Dusky | 24 | 11 | |
| Blue | 3 | 1 | |
| Black | 0 | 2 | |
| Visible peristalsis | | | |
| Present | 40 | 16 | $X^2 = 0.06, P = 0.80$* |
| Absent | 4 | 2 | |
| MA Doppler pulse | | | |
| Present | 32 | 8 | $X^2 = 1.7, P = 0.19$* |
| Absent | 12 | 10 | |
| Densitometry (indexed) | | | |
| Blue spectrum | 113 ± 2 units | 114 ± 4 units | $P = 0.37$** |
| Red spectrum | 124 ± 5 units | 117 ± 4 units | $P = 0.23$** |
| EMG (indexed) | 29 ± 3% | 23.8 ± 4% | $P \leq 0.047$** |
| FPSL | 31 ± 1.8 mA | 35 ± 0.2 mA | $P = 0.14$** |

TABLE 2

Normal vs Resection Margin Measurements for Quantitative Parameters

| Parameter | Normal bowel | Cutpoint |
|---|---|---|
| Densitometry | | |
| Red | 1.33 ± 0.20 units | 1.54 ± 0.04 units (P < 0.001) |
| Blue | 0.921 ± 0.14 units | 1.04 ± 0.02 units (P ≤ 0.002) |
| TSL | 22.7 ± 1.0 mA | 33.7 ± 1.7 mA (P < 0.001) |
| EMG | | |
| Proximal | 409 ± 35 mV | 110 ± 11 mV (P < 0.001) |
| Distal | 320 ± 37 mV | 83 ± 13 mV (P < 0.001) |

A doppler signal was audible in the marginal artery at 32 of the 44 resection margins in dogs that survived versus 8 of 18 margins in dogs that died. A Doppler pulse was present at 1 of the 2 resection margins in 18 of the 22 anastomoses that healed. Conversely, a Doppler signal was absent at both resection margins in 3 of the 9 anastomoses that leaked. Only three of five animals with audible Doppler signals at both resection margins survived.

Mean raw measurements of the three quantitative methods of viability assessment are shown in Table 2. The raw densitometry measurements in normal bowel were 0.921±0.14 units in the blue spectrum and 1.33±0.2 units in the red spectrum, both of which were significantly different than the mean raw densitometry measurements at the resection margins. However, there was no correlation between either the raw or the normalized reflection densitometry measurements and survival. Unnormalized reflection densitometry values in survivors and nonsurvivors are shown in Table 1. Mean raw densitometry measurements for the red and blue spectra in animals that survived were 1.55±0.05 and 1.03±0.03 units, respectively, versus mean values of 1.5±0.07 and 1.08±0.03 units in the red and blue spectra of nonsurvivors.

The mean TSL in normal bowel was 22.7±1.0 mA which was significantly lower than the mean TSL measured at the resection margins. However, there was no difference in mean TSL at the resection margins of animals that survived versus dogs that died.

The raw (unnormalized) EMG measured in normal bowel was significantly greater than the EMG measured respectively at the proximal and distal resection margins. The raw EMG in normal bowel proximal to the 40 cm ischemic segment was 409±35 mV versus 320±37 mV measured in normal bowel distal to the boundaries of the ischemic segment (P≦0.04 by paired Students t test). Moreover, the raw EMG measured at the proximal resection was 110±11 mV versus 83±13 mV measured at the distal cutpoint (P<0.001 by unpaired Students t test). These differences support normalizing the proximal and distal EMG measured at the resection margins with the EMG measured respectively in proximal and distal normal bowel. The proximal/distal normalized EMG measurements correlated with survival. Normalized EMG at the resection margin in survivors was 29±3% versus 23±4% in dogs that died (P≦0.047 by unpaired Students t test). Conversely, the raw (unnormalized) EMG at the resection margin in survivors was 97±11 mV versus 92±14 mV in nonsurvivors.

A primary goal of these experiments was to assess the. reliability of the quantified EMG measurements in predicting viability in ischemic bowel. Hence, three arbitrarily selected EMG measurements were used to determine the resection point. A total of 7 of 10 dogs in the first group died versus 1 of 10 in the second group and 1 of 11 in the third group. Survival in the second and third groups was significantly greater than that in the first group ($X^2$=12.0; P≦0.002). However, because only EMG was used to determine the point of resection and anastomosis, a two-way ANOVA was performed to evaluate the interaction between outcome (survival) in each of the three groups of dogs and the other quantitative methods of viability assessment (TSL, reflection densitometry). There was no significant method/outcome interaction using any of the other quantitative methods in the entire series of 31 dogs.

DISCUSSION

Intestinal ischemia is frequently a life-threatening condition that forces the surgeon to make rapid, arbitrary decisions regarding bowel viability during emergency operations performed in critically ill patients. Traditional methods of intraoperative bowel viability assessment have lacked sensitivity in accurate recognition of ischemic bowel and specificity in predicting long-term viability in bowel that appears ischemic. In the article *Intraoperative Determination of Small Intestinal Viability Following Ischemic Injury*, Ann. Surg. 193:628, 1990, Bulkley et al. clearly demonstrated this dilemma in a controlled prospective clinical study that compared the use of Doppler ultrasound, fluorescein fluorescence, and standard clinical judgment in 28 patients who had resection of 71 ischemic bowel segments in whom the operating surgeon determined the criteria for resection. Bulkley et al. found that the traditional methods of viability assessment were 90% accurate in determining long-term bowel viability but resulted in unnecessary bowel resection in 46% of cases.

In the present study, neither gross assessment of bowel color nor presence of visible peristalsis predicted anastomotic survival. These results are consistent with the results of previous experiments. Long-term viability is questionable in bowel that appears dusky or slightly cyanotic. In the present study, there are 24 resection margins that were classified as dusky but subsequently survived anastomosis. These findings are consistent with the results of Bulkley et al. which showed that standard clinical judgment is associated with a high rate of unnecessary resection when dusky-appearing bowel is removed.

In recent years, a variety of objective methods have been evaluated for use in intestinal viability assessment. Virtually all of these approaches have focussed on measurements of intestinal blood flow. Unfortunately, most of these techniques suffer from logistical shortcomings that preclude their use by the practicing surgeon. Use of fluorescein and radioactive microspheres requires intravenous injection of the materials and a waiting period of 5–10 minutes before measurements can be performed. In the article *Prediction of Viability of Revascularized Intestine with Radioactive Microspheres*, Surg. Gynecol. Obstet., 138:576, 1974, Zarins et al. noted that hyperemic or ischemic scans of labeled microspheres usually correlated with bowel viability, whereas a normal scan was frequently of little predictive value. Bulkley et al. reported greater sensitivity, specificity, and predictive accuracy using qualitative fluorescence patterns versus standard clinical judgment and Doppler ultrasound in patients with ischemic bowel. In two separate studies, as revealed in the articles *Quantification of Fluorescein Distribution to Strangulated Rat Ileum*, J. Surg. Res., 34:179, 1983, and *Monitoring Tissue Elimination of Fluorescein with the Perfusion Fluorometer: A New Method to Assess Capillary Blood Flow*, Surgery, 90:409, 1981, Silverman et al. found that quantitative fluorometry using a perfusion fluorometer had greater positive and negative predictive accuracy than either clinical judgment or qualitative fluorometry using a Wood's lamp. Although hydrogen gas clearance provides an accurate measurement of submucosal blood flow, its clinical usefulness is limited by the potential for tissue damage by electrode penetration into the bowel wall.

Doppler ultrasound has gained wide acceptance as an adjunctive modality in bowel viability assessment. The popularity of Doppler ultrasound is primarily due to its inherent simplicity and its availability in the standard hospital operating room. However, the reliability of Doppler ultrasound in intestinal viability assessment has been inconsistent. In the article *Determination of Viability of Ischemic Intestine by Doppler Ultrasound*, Surgery, 83:705, 1978, Cooperman et al. resected ischemic bowel at the site of the last audible Doppler signal in the bowel wall and had a 100% survival rate after 1 month. Likewise, as stated in the article *Prediction of Intestinal Viability Using Doppler Ultrasound Techniques*, Am. J. Surg., 129:642, 1975, Wright and Hobson demonstrated that an audible Doppler pulse in the serosa and mesentery correlated with late intestinal viability. Conversely, Bulkley et al. reported that doppler ultrasound did not increase the accuracy of intestinal viability determination beyond that provided by conventional clinical judgment. In earlier studies, the presence of an audible Doppler signal in the marginal artery at the anastomotic site correlated with long-term bowel viability. However, in the present study there was no correlation between an audible Doppler signal in the marginal artery and survival. Given these inconsistent results, Doppler ultrasound should be used with caution in intraoperative assessment of intestinal viability.

Reflection densitometry has not been previously studied in experimental models of intestinal ischemic disease. This technology was designed for use in the printing industry for quantitative determination of color print quality. Although the instrument was not intended for in vivo use, the densitometer was adapted for use in live tissue by covering the lens with cellophane to prevent deposition of blood and body fluids. Reflection densitometry measurements in the red and blue spectrum did not predict anastomotic survival. However, it is interesting to note that measurements in the blue spectrum were virtually the same in dogs that survived versus those that died, whereas measurement in the red spectrum were higher in dogs that survived versus those that died. These results suggest that there may be only a small amount of light reflection relative to absorption in grossly cyanotic bowel. Reflection densitometry appears to be more accurate in mildly ischemic bowel that retains a reddish color (to the naked eye) in comparison with more severely ischemic bowel which appears grossly cyanotic. Further refinements in this technology are necessary before reflection densitometry can be used clinically in intestinal viability assessment.

In previous experiments it was found that TSL measured by the ECM was a reliable method of bowel viability assessment. However, in the present study TSL did not correlate with anastomotic survival. The lack of correlation between TSL and survival is probably due to several factors. First, there occasionally is difficulty in distinguishing low-amplitude smooth muscle contractions in ischemic bowel from baseline artifact on the strip chart recorder. Another drawback of the TSL measurements is the need for multiple stimulation response trials until the lowest measurable contractile response is elicited.

Given the shortcomings of the TSL measurements, the capability of quantitative EMG measurements was added to the ECM. In the article *The Effect of Ischemia on Intestinal Nerves and Electrical Slow Waves*, Am. J. Dig. Dis., 15:959, 1970, Daniel and Kyi showed that prolonged ischemia in the bowel resulted in smooth muscle damage and permanent changes in intrinsic myoelectric activity. These findings are supported by the work of other investigators who demonstrated that prolonged ischemia resulted in reduction of both slow wave coupling and frequency. This knowledge provided the basis for constructing a computer algorithm that quantified intrinsic EMG activity without direct stimulation to the bowel. Since the quantitative EMG measurements were made before any electrical stimuli were applied to the bowel, the likelihood of stimulation induced artifact was thereby eliminated.

The EMG data were analyzed by normalizing measurements obtained in normal bowel proximal and distal to the boundaries of the 40 cm ischemic segment with the respective EMG measurements at the proximal and distal resection margins. This methodology compensates for the inherent differences in myoelectric activity that are produced by the central area of severe ischemia or necrosis in the model of arterial occlusion. Previous investigators have shown in dogs that transection of the small bowel results in significant decreases in slow wave frequency as well as unmasking of an intrinsic pacesetter potential in the bowel distal to the transection site. The intrinsic frequency of the basal electrical rhythm in the bowel distal to the cutpoint was consistently lower than that in the bowel proximal to the transection site.

In the present study severe segmental ischemia or necrosis in the small bowel likewise resulted in unmasking of a slower intrinsic pacesetter potential in viable bowel distal to the region of ischemic damage. Use of proximal- versus distal-normalizing of the EMG data was validated by the significantly greater EMG measurements in the proximal normal bowel versus distal normal bowel. Mean EMG measurements at the proximal resection margins were also significantly greater than those at the distal resection margins. Conversely, comparison of mean EMG measurements at the resection margin without proximal- versus distal-normalizing disclosed no significant difference between survivors (97 ±10 mV) and nonsurvivors (92±14 mV). Hence, the inherently slower pacesetter potential in bowel distal to an area of severe ischemia must be accounted for in using quantitative EMG measurements in assessment of viability in ischemic bowel.

The experimental protocol was designed to learn whether a numerical viability threshold could be determined for the quantified EMG measurements. However, the last dog in the third group died of further bowel necrosis. Moreover, there was considerable overlap of both the raw and normalized EMG measurements in the second and third groups, which precluded establishment of a narrow numerical range that consistently predicted survival or death. Thus, refinement of the computer algorithm used to quantify the EMG should improve the specificity of these measurements.

In summary, quantitative EMG measurements using the ECM probe provided an accurate assessment of long-term viability in this arterial ligation model of intestinal ischemia. The EMG measurements were more reliable than quantitative color measurements using reflection densitometry and three traditional parameters of viability assessment: peristalsis, color, and marginal artery Doppler ultrasound. Quantitative myoelectric measurements may eventually be useful in clinical determination of bowel viability.

With the present invention instrument 10 now fully described, it can thus be seen that the primary object set forth above is efficiently attained and, since certain changes may be made in the above-described instrument 10 without departing from the scope of the invention, it is intended that all matter contained in the above description or shown in the accompanying drawings shall be interpreted as illustrative and not in a limiting sense.

What is claimed is:

1. A medical instrument which quantifies the survivability of tissue, said medical instrument comprising:
    a measurement probe having gripping means for gripping tissue, stimulus electrodes for delivering an electrical stimulus, means for sensing movement in tissue gripped by said measurement probe in response to said electrical stimulus, and measurement electrodes for sensing electromyographic activity in tissue gripped by said measurement probe, wherein said stimulus electrodes, said measurement electrodes, and said tissue movement sensing means are mounted on said gripping means;
    control means for controlling the generation of said electrical stimulus, for recording and analyzing movement sensed by said tissue movement sensing means and electromyographic activity sensed by said measurement electrodes, and for generating at least one quantity which is representative of the survivability of the tissue as indicated by at least one of the sensed tissue movement and the sensed electromyographic activity; and
    circuit means for electrically connecting said measurement probe with said control means and processing electrical signals representing said electrical stimulus, said electromyographic activity, and said tissue movement.

2. The medical instrument defined in claim 1, further comprising means for sensing movement of said measurement probe.

3. The medical instrument defined in claim 1, wherein said measurement probe includes said means for sensing movement of said measurement probe, wherein said control means records and analyzes movement sensed by said probe movement sensing means, and wherein said circuit means processes at least one electrical signal representing said probe movement.

4. The medical instrument defined in claim 3, wherein said control means the movement sensed by said probe movement sensing means out of the movement sensed by said means for sensing movement in tissue gripped by said measurement probe in response to said electrical stimulus with a noise cancellation weighted subtraction procedure thereby providing a rectified, noise canceled contractile response.

5. The medical instrument defined in claim 4, wherein said control means calculates a difference between the rectified, noise canceled contractile response and a recorded normal contractile response with a weighted subtraction procedure.

6. The medical instrument defined in claim 5, wherein said control means calculates a root mean square of the difference thereby generating a number which quantifies the survivability of the tissue gripped by said measurement probe.

7. The medical instrument defined in claim 1, wherein said gripping means further comprises a clamp for gripping tissue.

8. The medical instrument defined in claim 7, wherein said clamp comprises a rigid support member and a flexible support member, wherein said rigid support member and said flexible support member are biased against each other so as to allow tissue movement to be gripped therebetween, and wherein said tissue sensing means comprises means for sensing bending in said flexible support member.

9. The medical instrument defined in claim 8, wherein said tissue movement sensing means is a strain gauge movement transducer.

10. The medical instrument defined in claim 7, wherein said clamp comprises a pair of rigid support members, wherein said rigid support members are biased against each other so as to allow tissue to be gripped therebetween, and wherein said tissue movement sensing means comprises means for sensing pressure applied against said rigid support members.

11. The medical instrument defined in claim 10, wherein said tissue movement sensing means comprises a flexible fluid filled membrane and a pressure transducer, wherein both said flexible fluid filled membrane and said pressure transducer are mounted on one of said rigid support members, and wherein said pressure transducer senses changes in pressure in said flexible fluid filled membrane.

12. The medical instrument defined in claim 1, wherein said control means calculates a root mean square of the electromyographic activity over a selected time interval, thereby generating a number which quantifies the survivability of the tissue gripped by said measurement probe.

13. The medical instrument defined in claim 1, wherein said control means filters out a slow wave component or spike from the electromyographic activity, thereby producing a de-spiked EMG signal.

14. The medical instrument defined in claim 13, wherein said control means filters out one or more frequency components from the de-spiked EMG signal.

15. The medical instrument defined in claim 14, wherein said control means calculates a root mean square of the frequency-filtered, de-spiked EMG signal, thereby generating a number which quantifies the survivability of the tissue gripped by said measurement probe.

16. A medical instrument which quantifies the survivability of tissue, said medical instrument comprising:

a measurement probe having gripping means for gripping tissue, stimulus electrodes for delivering an electrical stimulus, means for sensing movement in tissue gripped by said measurement probe in response to said electrical stimulus, and measurement electrodes for sensing electromyographic activity in tissue gripped by said measurement probe, wherein said stimulus electrodes, said measurement electrodes, and said tissue movement sensing means are mounted on said gripping means; and control means for controlling the generation of said electrical stimulus, for recording and analyzing movement sensed by said tissue movement sensing means and electromyographic activity sensed by said measurement electrodes, and for generating at least one quantity which is representative of the survivability of the tissue as indicated by at least one of the sensed tissue movement and the sensed electromyographic activity.

17. The medical instrument defined in claim 16, further comprising means for sensing movement of said measurement probe.

18. The medical instrument defined in claim 16, wherein said measurement probe includes said means for sensing movement of said measurement probe, and wherein said control means records and analyzes movement sensed by said probe movement sensing means.

19. The medical instrument defined in claim 18, wherein said control means filters the movement sensed by said probe movement sensing means out of the movement sensed by said means for sensing movement in tissue gripped by said measurement probe in response to said electrical stimulus with a noise cancellation weighted subtraction procedure thereby providing a rectified, noise canceled contractile response.

20. The medical instrument defined in claim 19, wherein said control means calculates a difference between the rectified, noise canceled contractile response and a recorded normal contractile response with a weighted subtraction procedure.

21. The medical instrument defined in claim 20, wherein said control means calculates a root mean square of the difference thereby generating a number which quantifies the survivability of the tissue gripped by said measurement probe.

22. The medical instrument defined in claim 16, wherein said gripping means further comprises a clamp for gripping tissue.

23. The medical instrument defined in claim 22, wherein said clamp comprises a rigid support member and a flexible support member, wherein said rigid support member and said flexible support member are biased against each other so as to allow tissue to be gripped therebetween, and wherein said tissue movement sensing means comprises means for sensing bending in said flexible support member.

24. The medical instrument defined in claim 23, wherein said tissue movement sensing means is a strain gauge movement transducer.

25. The medical instrument defined in claim 22, wherein said clamp comprises a pair of rigid support members, wherein said rigid support members are biased against each other so as to allow tissue to be gripped therebetween, and wherein said tissue movement sensing means comprises means for sensing pressure applied against said rigid support members.

26. The medical instrument defined in claim 25, wherein said tissue movement sensing means comprises a flexible fluid filled membrane and a pressure transducer, wherein both said flexible fluid filled membrane and said pressure transducer are mounted on one of said rigid support members, and wherein said pressure transducer senses changes in pressure in said flexible fluid filled membrane.

27. The medical instrument defined in claim 16, wherein said control means calculates a root mean square of the electromyographic activity over a selected time interval, thereby generating a number which quantifies the survivability of the tissue gripped by said measurement probe.

28. The medical instrument defined in claim 16, wherein said control means filters out a slow wave component or spike from the electromyographic activity, thereby producing a de-spiked EMG signal.

29. The medical instrument defined in claim 28, wherein said control means filters out one or more frequency components from the de-spiked EMG signal.

30. The medical instrument defined in claim 29, wherein said control means calculates a root mean square of the frequency-filtered, de-spiked EMG signal, thereby generating a number which quantifies the survivability of the tissue gripped by said measurement probe.

* * * * *